United States Patent [19]
Gray et al.

[11] Patent Number: 5,566,479
[45] Date of Patent: Oct. 22, 1996

[54] SHOE CONTRUCTION FOR USE BY DIABETIC PERSONS

[76] Inventors: Frank B. Gray, 5104 Lyons View Dr., Knoxville, Tenn. 37919; John L. Parris, 314 Kennon Rd., Knoxville, Tenn. 37909; Rainer G. Riffert, 3804 Oakhurst Dr., Knoxville, Tenn. 37979

[21] Appl. No.: 407,689

[22] Filed: Mar. 21, 1995

[51] Int. Cl.⁶ .............................. A43B 23/00; A61B 5/00
[52] U.S. Cl. ..................... 36/137; 36/1; 36/136; 36/139; 73/172; 128/779
[58] Field of Search .................... 36/137, 139, 136, 36/140, 1; 73/172; 128/779

[56] References Cited

U.S. PATENT DOCUMENTS

| | | | |
|---|---|---|---|
| 2,290,387 | 7/1942 | Schwartz | 73/151 |
| 4,092,633 | 5/1978 | Fletcher et al. | 340/213 R |
| 4,136,682 | 1/1979 | Pedotti | 128/2 S |
| 4,178,916 | 12/1979 | McNamara | 128/734 |
| 4,179,692 | 12/1979 | Vance | 340/573 |
| 4,195,643 | 4/1980 | Pratt, Jr. | 128/779 |
| 4,365,637 | 12/1982 | Johnson | 128/734 |
| 4,426,884 | 1/1984 | Polchanioff | 73/172 |
| 4,554,930 | 11/1985 | Kress | 73/172 |
| 4,647,918 | 3/1987 | Goforth | 340/573 |
| 4,858,620 | 8/1989 | Sugarman et al. | 73/172 |
| 5,253,654 | 10/1993 | Thomas et al. | 128/779 |
| 5,269,081 | 12/1993 | Gray | 36/136 |
| 5,323,650 | 6/1994 | Fullen et al. | 128/779 |
| 5,357,696 | 10/1994 | Gray et al. | 36/136 |
| 5,373,651 | 12/1994 | Wood | 36/136 |
| 5,408,873 | 4/1995 | Schmidt et al. | 128/779 |

*Primary Examiner*—Paul T. Sewell
*Assistant Examiner*—Marie Denise Patterson
*Attorney, Agent, or Firm*—Pitts & Brittian, P.C.

[57] ABSTRACT

A shoe to be worn by diabetic persons, or persons afflicted with various types of foot maladies, where excess pressure exerted upon a portion of the foot tends to give rise to ulceration. The shoe body is fabricated to have relieved areas in the inner surface that contacts the foot at locations where the excess pressure is thought to possibly occur. Mounted within each relieved area is a force sensing resistor unit that is connected to a switching circuit. When the switching circuit senses a pressure against the force sensing resistor of a value corresponding to a set threshold, the switching circuit causes the energization of an alarm unit to warn the wearer of the existence of this threshold pressure. At this point in time, the wearer can remove the shoe to prevent the damage to the foot. Provision can be made to adjust the critical threshold pressure at which the alarm is given.

17 Claims, 3 Drawing Sheets

SHOE CONTRUCTION FOR USE BY DIABETIC PERSONS

TECHNICAL FIELD

The present invention relates to shoes for use by patients with a foot malady who experience a detrimental effect upon the malady by undue localized pressure, and more particularly to a shoe construction for use by diabetic persons where dangerous lesions are often created by the excess localized pressure. The present invention monitors the pressure at locations where the excess pressure might occur, and provides a warning to the wearer when a threshold pressure is reached such that the wearer can remove the shoe before damage occurs to the foot.

BACKGROUND ART

In the United States alone, there are approximately thirteen million persons who have diabetes, with about 750,000 new cases diagnosed each year. Total health care costs for diabetes mellitus is about 20 billion dollars per year, representing 5% of the total health care dollar.

Among the many problems that diabetic patients face, foot ulceration is one of the more significant risks. When it occurs, it leads to increased morbidity, amputation rates and mortality. For example, incidents of amputation resulting from ulceration is fifteen times higher than found in the general population. This is primarily because of the poor healing potential seen in the diabetic patient. Ulceration of the foot is multi-factorial in the diabetic population, and among the pre-disposing etiologies are: small vessel disease leading to ease of skin breakdown and poor healing potential; a peripheral neuropathy which makes the foot insensitive to pain; and, in many cases, a suppressed immunologic system.

It has been appreciated for some time that potential pressure areas of the foot can be identified by cast molding or electronic mapping techniques. With this information custom shoes or orthoses can be fabricated which are provided with relieved areas created by contouring that portion of the shoe away from the defined potential pressure areas. However, shoe configurations tend to change with wear and foot shapes vary with modes of force distribution. For example, activity levels, edema and subtle changes in gait pattern create contact in the area that was meant to be protected. Often the patient may be unaware of the change due to the loss of protective sensation. Thus, what was meant to be a protected area actually may ulcerate. Such changes may occur in a brief time frame of only a few hours of wear of the custom shoe.

It will be recognized that similar problems with undue pressure, and the resulting ulceration, may occur with various forms of foot maladies. For example, persons with partially amputated feet often can have undue pressure applied within the shoe, with the locations changing in the same manner as described above. Persons with a club foot or other deformities likewise can have ulceration problems.

A multi-event notification system for monitoring critical pressure points on persons with diminished sensation of the feet is described in U.S. Pat. No. 4,647,918 issued to W. Goforth on Mar. 3, 1987. This system utilizes a plurality of pressure transducers mounted within a shoe for measuring and monitoring pressure at any number of points on a patient's foot. The transducers are electrically connected to a microprocessor that is programmable to integrate the pressure sensed at the sensing points over a preselected time interval. If the integrated pressure at any of the sensing points reaches a preselected threshold over this time interval, an alarm indicator provides an alarm indication that the total number of pressure events exceeds the threshold limit.

Further, there are devices that provide some form of alarm when foot pressure against the bottom of a shoe exceeds a certain threshold. These devices include those described in U.S. Pat. 5,253,654 issued to B. Thomas et al on Oct. 19, 1993, and U.S. Pat. Nos. 5,269,081 and 5,357,696 issued to the present inventors on Dec. 14, 1993 and Oct. 25, 1994, respectively. These patents, and certain others cited therein, deal with monitoring the force being applied to a foot to ascertain the proper force for promoting healing of a patient after hip or knee surgery or injury.

None of the above-cited patents describes a simple system for providing a signal to a person when adverse pressure is applied to any portion of the foot, this adverse pressure potentially causing ulceration. Further, none is specifically designed to be incorporated into special shoes fabricated with relieved inner portions to minimize excess pressure.

Therefore it is an object of the present invention to provide a shoe for use by persons having a foot malady wherein a simple and thus inexpensive monitoring system is utilized to provide a warning to the wearer that excess pressure has been generated at potentially dangerous positions.

Another object of the present invention is to provide a shoe for use by diabetic persons wherein relieved areas are provided in the inner surface of the shoe to reduce pressure at selected regions, with a simple monitoring system associated with these relieved areas to monitor for pressures in excess of those desired in such areas.

It is a further object of the present invention to provide a shoe for use by diabetic persons wherein at least one relieved area is provided in the inner surface of the shoe to reduce pressure at this area, with a force sensing resistor detector being provided beneath the relieved area(s), the force sensing resistor detector being a portion of an electrical circuit such that a signal is generated when excess pressure is detected by the force sensing resistor.

It is also an object of the present invention to provide a shoe for use by diabetic persons wherein at least one relieved area is provided in the inner surface of the shoe to reduce pressure at this at least one area, with a force sensing resistor detector being provided beneath the relieved area(s), the force sensing resistor detector being a portion of an electrical circuit such that a visible signal is instantaneously generated on the outer surface of the shoe when excess pressure is detected by the force sensing resistor.

It is also an object of the present invention to provide a shoe for use by diabetics and other persons with potential detrimental effects of excess pressure against the foot wherein the threshold pressure to cause a warning to the wearer can be adjusted.

These and other objects of the present invention will become apparent upon a consideration of the drawings referred to hereinafter and a complete description thereof.

SUMMARY OF THE INVENTION

In accordance with the objects of the present invention there is provided a shoe for diabetic persons, and patients having other foot maladies, to detect pressures being applied to the foot that may result (if not removed) in ulceration of the foot in the area of excess pressure. The invention specifically is applied to shoes wherein internal relieved areas are provided to normally reduce pressure to the foot at the locations of these relieved areas. A force sensing resistor element is placed within any relieved area that is provided such that should excess pressure be generated between the shoe inner surface and the foot, a signal will be instantaneously generated that warns the wearer that such excess pressure exists or is approached. With such warning, the wearer can remove the shoe prior to ulceration occurring. Such monitoring is especially helpful for diabetic patients because they are very prone to ulceration with its often very serious consequences.

BEST MODE FOR CARRYING OUT THE INVENTION

Figure 1:
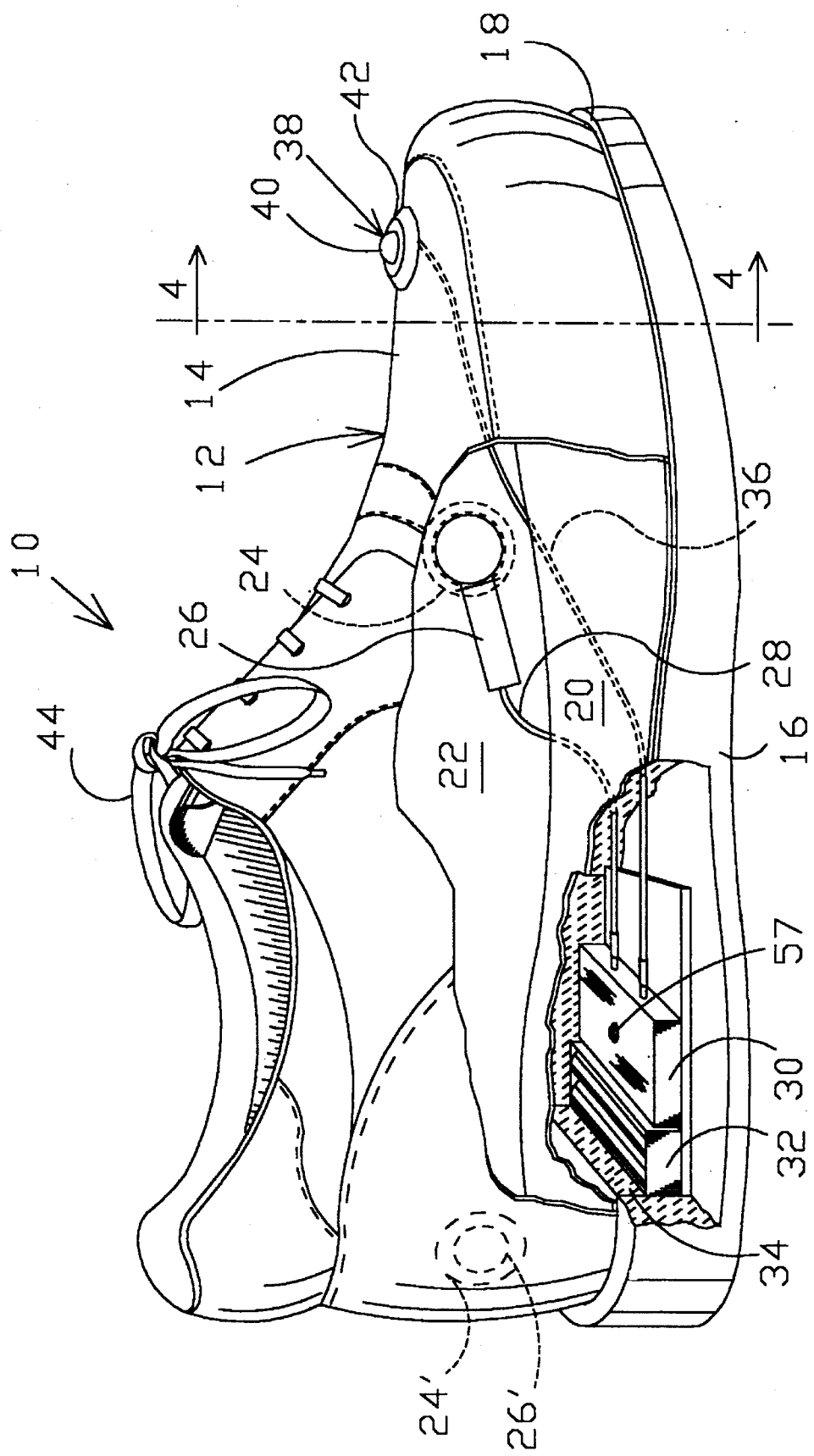
FIG. 1 is a drawing depicting a shoe of the present invention, partially cut away, according to the objects of the present invention.

A shoe constructed according to one embodiment of the present invention is shown at 10 in FIG. 1. This device has a shoe body 12 made up of a shoe "upper" 14 and a shoe sole 16 joined by any suitable means as at 18. Suitable means is provided for fastening the shoe 10 to the foot of a wearer: illustrated is a typical shoelace 44.

The sole 16 defines, or is provided with, an inner sole 20, and the upper 14 defines an inner surface 22. Both the inner sole 20 and the inner surface 22 of the upper typically are covered so as to provide a smooth surface relative to the foot of a wearer. For a diabetic shoe, or any shoe where pressure is to be reduced at a specified location, the inner surface 22, and/or in some instances the inner sole 20, is provided with at least one relieved area 24. Although the relieved area 24 illustrated in FIG. 1 is shown as being circular, it can have any configuration (including depth) to accomplish the reduction of shoe/foot pressure. It will be recognized from a discussion hereinafter that there can be several relieved areas each at different locations within a given shoe depending upon whether there is a singular location to reduce pressure or multiple locations where this function is desired (see FIGS. 1 and 4). The relieved area(s) 24 is (are) prepared using techniques known to those who manufacture this type of specialized shoe.

Mounted beneath (or at) the inner surface 22 at each relieved area 24 is a force sensing resistor unit 26 to monitor pressure between the inner surface 22 at the relieved area 24 and a foot of a wearer (not shown). This force sensing resistor unit (FSR) is typically a Model 303 manufactured by Interlink Electronics of Camarillo, Calif., and is connected by leads to a switching circuit 30 and a power source 32. Typically this switching circuit 30 and the power source (e.g., batteries) 32 are mounted within a cavity 34 in the shoe sole 16. Output leads 36 connect the switching circuit 30 to a lamp unit 38 of any suitable type having a lamp 40 with a light emission sufficient to be seen by a wearer of the shoe 10. The lamp unit 38 contains, in a preferred embodiment, a switch unit 42 to de-energize the lamp 40 when desired. Of course, it will be understood that the switch unit 42 can be a separately mounted element on the shoe 10 at a location that can be reached by a wearer (see FIG. 3). Further, it will be understood that the leads 28 and 36 are typically sized and positioned so as to prevent pressure on the surface of the wearer's foot.

Figure 2:
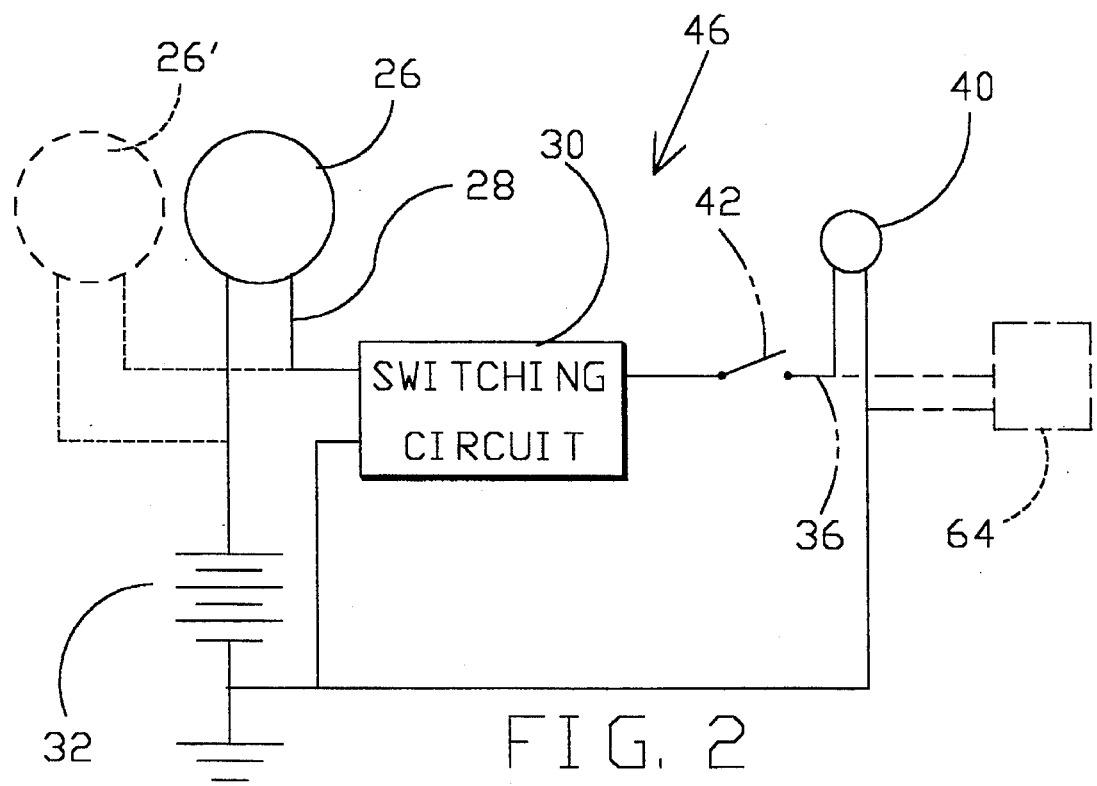
FIG. 2 is a block diagram of the electrical circuit of the present invention.

A circuit 46 for use with the shoe 10 of FIG. 1 is illustrated in FIG. 2. The force sensing resistor 26 controls the current flow into the switching circuit 30 from the power source 32. As pressure is applied to the force sensing resistor, current is caused to flow. The switching circuit 30 detects when this current corresponds to a threshold of pressure occurs. At this point of threshold detection, the switching circuit 30 is connected to the lamp 40 so as to illuminate the same. Typically the lamp is a LED. The power to the lamp 40 can be continuous, and thus cause the lamp 40 to be illuminated constantly, or the lamp can flash intermittently so that the lamp 40 flashes to gain the attention of the wearer of the shoe 10. Circuitry within the switching circuit 30 to accomplish these functions will be well known to persons skilled in the art, with one embodiment shown in FIG. 3. In order to minimize drain on the power source 32, the switch 42 permits de-energization. This switch 42 can be positioned within various locations within the circuit 46 as will be understood by persons skilled in the art.

Figure 3:
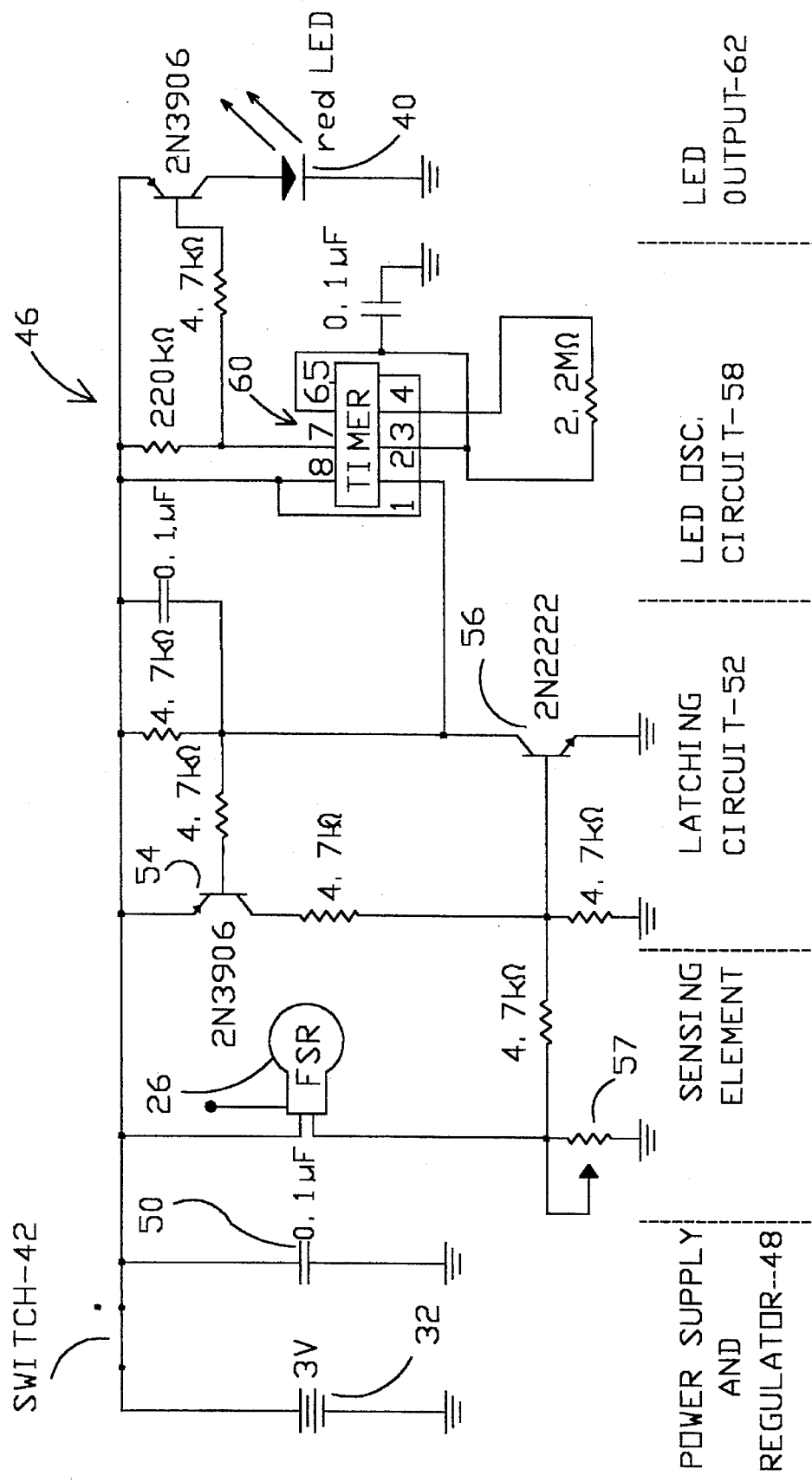
FIG. 3 is a circuit diagram of one embodiment of the present invention.

A schematic circuit drawing of one embodiment of the circuit 46 of FIG. 2 is illustrated in FIG. 3. A "power supply and regulator" 48 includes the battery 32 and a capacitor 50. The "sensing element" is the force sensing resistor unit 26, and a "latching circuit" 52 includes transistors 54, 56 and associated resistors and capacitors as illustrated. In a preferred embodiment, an adjustable resistor 57 is provided whereby the threshold pressure for causing operation of the latching circuit can be adjusted. This typically would be located with other circuit means 30 in the sole of the shoe where it can be set by a clinician (see FIG. 1). The "latching circuit" 52 controls the operation of a "LED oscillating circuit" 58 utilizing a timer 60, and thus provides intermittent power to the LED 40 in the "LED output" 62. The "latching circuit" 52 and the "LED oscillating circuit" 58, and their operation, will be known to persons skilled in the art and the circuits illustrated are only illustrative of circuits to perform the desired functions.

With regard to the operation of circuit 46 of FIG. 3, the FSR initiates the latching circuit 52. This, in turn, powers up the timer 60 of the oscillating circuit 58 causing the LED 40 to blink. This will continue until the circuit 46 is "reset" by the opening of switch 42, and then reclosing the switch 42, so that the circuit 46 is in a "ready" condition. Of course, if the battery 32 power becomes sufficiently low, the operation of circuit 46 ceases. Since the battery drain is very low, the circuit 46 can be retained in the "ready" condition for long periods of time.

Figure 4:
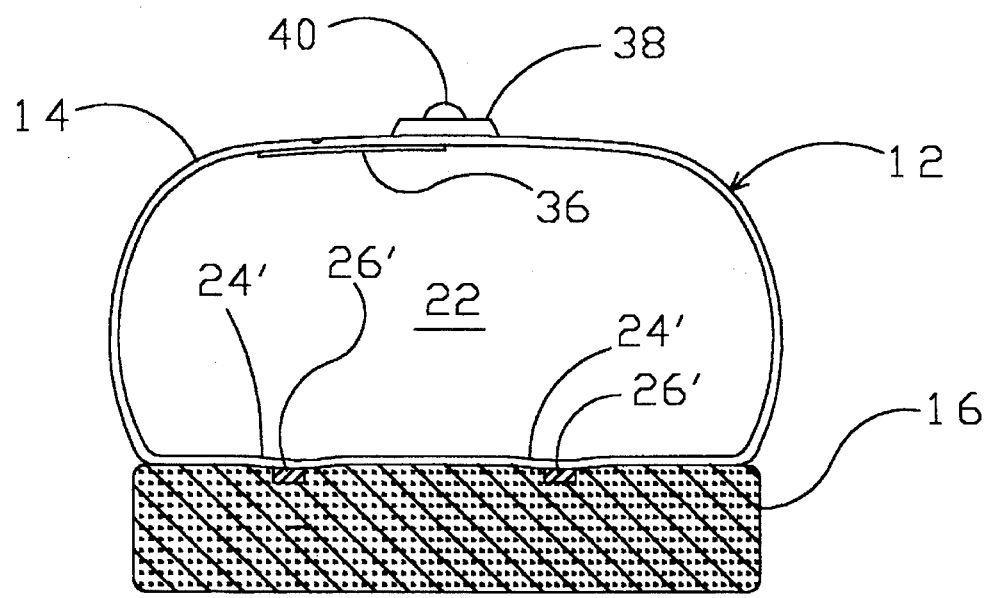
FIG. 4 is a partial cross-sectional drawing of a shoe illustrating typical additional positions for locating a sensor of the type illustrated in FIGS. 2 and 3, taken at 4—4 of FIG. 1.

In the event several locations within the shoe 10 are to be monitored for pressure, additional force sensing resistor units 26 are placed beneath each of the relieved areas 24 of the shoe 10. This is indicated in FIGS. 2 and 4 by another force sensing resistor unit 26' shown in phantom beneath recessed area 24'. In this event, the switching circuit 30 can include circuit means to respond to the highest pressure signal from the various force sensing resistors 26. Alternatively, each force sensing resistor unit 26, 26') can be connected to its own circuit means and lamp and thus operate independently to provide a signal to the wearer.

In accordance with the present invention, a shoe body 12 is fabricated for a specific application. The interior surface (20 and/or 22) is contoured to provide the desired relieved areas 24. This is accomplished by the same techniques well known in the art. Typically electronic mapping or cast forming are utilized to determine the specific shape of the interior of the shoe 10. During the course of forming the shoe sole 16, a cavity 34 is formed as illustrated in FIG. 1. Thereafter, a force sensing resistor unit 26 is positioned beneath each relieved area 24 and connected to the switching circuit 30 as well as to the lamp unit 38. The switching circuit 30 is set so as to illuminate the lamp 40 when the pressure against the force sensing resistor unit 26 reaches a selected threshold. This illumination can be continuous or intermittent, as discussed above. When the lamp 40 becomes illuminated, the wearer can remove the shoe to prevent the detected pressure from causing damage to the foot. The switch 42 can be operated at this time to stop any drain on the power source 32.

There may be applications where an audible sound is desired rather than a visible signal that the pressure threshold has been reached. This might be the case for sight-handicapped persons. Thus, a sound-producing device 64 can be substituted for the lamp 40. Such a device is illustrated in FIG. 2 in phantom lines. Also, although not shown, a low power, low frequency transmitter can be incorporated into the switching circuit 30 to transmit a signal to a receiver worn on other parts of the patient's body.

From the foregoing, it will be understood that an improved and simplified system has been incorporated into a shoe to be worn by a diabetic patient—or a patient with other foot maladies. This provides an warning instantly to the patient that a threshold pressure has been applied to sensitive portions of the foot such that the shoe can be removed before the excess pressure causes ulceration. Provision is made to adjust this threshold pressure. Although certain typical elements are identified, these are for illustration and not for a limitation of the invention. The invention is to be limited only by the appended claims and their equivalents.

We claim:

1. A shoe for use by a person having a foot malady located in at least one site of the foot of the person where a pressure in excess of a critical threshold pressure has a detrimental effect on the malady, the shoe comprising:

a shoe body to substantially enclose the foot of the person, said shoe body defining an interior surface to contact the foot, said interior surface provided with a relieved region in the at least one site to reduce pressure directed against the foot at said site;

a force sensing resistor unit positioned beneath each said relieved region;

a power source;

a switch circuit connecting said force sensing resistor unit and said power source, said switch circuit detecting current flow through said force sensing resistor unit as a function of the pressure applied to said force sensing resistor unit, and providing an instantaneous output signal when the pressure exceeds the critical threshold; and an indicator means connected to said switch circuit to receive said instantaneous output signal to provide a signal to the person when the pressure in excess of the critical threshold is applied to said force sensing resistor unit at the location where the pressure is detrimental to the malady.

2. The shoe of claim 1 wherein said switch circuit includes a latching means to maintain said switch circuit in an ON position when the pressure against said force sensing resistor unit exceeds the critical threshold pressure and said indicator means produces a continuous signal to the person until said switch circuit is manually switched to an OFF position.

3. The shoe of claim 1 wherein said switch circuit includes a latching means to maintain said switch circuit in an ON position when the pressure against said force sensing resistor unit exceeds the critical threshold pressure and said indicator means produces an intermittent signal to the person until said switch circuit is manually switched to an OFF position.

4. The shoe of claim 1 wherein said switch circuit is connected to said indicator means by transmission means for providing said signal to the person from said indicator means.

5. The shoe of claim 1 wherein said indicator means activates a visual signal device to provide a visual signal to the person.

6. The shoe of claim 1 wherein said indicator means activates an audible sound device to provide an audible signal to the person.

7. The shoe of claim 1 wherein said switch circuit includes means for adjusting a value of the critical threshold pressure.

8. A shoe for use by a person afflicted by diabetes where lesions are formed on the person's foot at a site in at least one location of the foot where a pressure in excess of a threshold critical pressure has a detrimental effect on the forming of the lesions, the shoe comprising:

a shoe body to substantially enclose the foot of the person, said shoe body defining an interior surface to contact the foot, said interior surface provided with a relieved region at said at least one site to reduce pressure directed against the foot at said site;

a force sensing resistor unit positioned beneath said relieved region;

a power source;

a switch circuit connecting said force sensing resistor unit and said power source, said switch circuit detecting current flow through said force sensing resistor unit as a function of the pressure applied to said force sensing resistor unit, and providing an instantaneous output signal when the pressure exceeds the critical threshold; and an indicator means connected to said switch circuit to receive said instantaneous output signal to provide a signal to the person when the pressure in excess of the critical threshold is applied to said force sensing resistor unit where the pressure is detrimental to the forming of the lesions.

9. The shoe of claim 8 wherein said switch circuit includes a latching means to maintain said switch circuit in an ON position when the pressure against said force sensing resistor unit exceeds the critical threshold pressure and said indicator means produces a continuous signal to the person until said switch circuit is manually switched to an OFF position.

10. The shoe of claim 1 wherein said switch circuit includes a latching means to maintain said switch circuit in an ON position when the pressure against said force sensing resistor unit exceeds the critical threshold pressure and said indicator means produces an intermittent signal to the person until said switch circuit is manually switched to an OFF position.

11. The shoe of claim 8 wherein said switch circuit is connected to said indicator by transmission means for providing said signal to the person from said indicator means.

12. The shoe of claim 8 wherein said indicator means activates a visual signal device to provide a visual signal to the person.

13. The shoe of claim 8 wherein said indicator means activates an audible sound device to provide an audible signal to the person.

14. The shoe of claim 8 wherein said switch circuit comprises a latching circuit operated by a signal from said force sensing resistor unit, and an oscillating circuit energized by said latching circuit whereby said indicator is energized intermittently.

15. The shoe of claim 8 wherein said switch circuit includes means for adjusting a value of the critical threshold pressure.

16. A shoe for use by a person afflicted by diabetes where lesions are formed on the person's foot at a site in at least one location of the foot where a pressure in excess of a threshold critical pressure has a detrimental effect on the forming of the lesions, the shoe comprising:

a shoe body to substantially enclose the foot of the person, said shoe body defining an interior surface to contact the foot, said interior surface provided with a relieved region at said at least one site to reduce pressure directed against the foot at said site;

a force sensing resistor unit positioned beneath said relieved region;

a battery power source contained within said shoe body;

a switch circuit connecting said force sensing resistor unit and said power source, said switching circuit detecting current flow through said force sensing resistor unit as a function of the pressure applied to said force sensing resistor unit and providing an instantaneous output signal when the pressure exceeds the critical threshold, said switch circuit including a latching circuit for receiving and being operated by said output signal, said switch circuit further including an oscillating circuit operated by said latching circuit, said switch circuit contained within said shoe body; and a visual indicator means on an exterior surface of said shoe body connected to said oscillating circuit to provide a signal to the person when the pressure in excess of the critical threshold is applied to said force sensing resistor unit where the pressure is detrimental to the forming of the lesions.

17. The shoe of claim 6 wherein said switch circuit further includes means for preadjusting a value of the critical threshold pressure.

\* \* \* \* \*